US00PP33485P2

(12) United States Plant Patent
Ohde

(10) Patent No.: US PP33,485 P2
(45) Date of Patent: Sep. 14, 2021

(54) ***LIPPIA* PLANT NAMED 'ECOLOPIA3'**

(50) Latin Name: *Lippia nodiflora*
Varietal Denomination: ECOLOPIA3

(71) Applicant: Masataka Ohde, Oyama (JP)

(72) Inventor: Masataka Ohde, Oyama (JP)

( * ) Notice: Subject to any disclaimer, the term of this patent is extended or adjusted under 35 U.S.C. 154(b) by 0 days.

(21) Appl. No.: 17/065,796

(22) Filed: Oct. 8, 2020

(51) Int. Cl.
*A01H 5/12* (2018.01)
*A01H 6/50* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new and distinct cultivar of *Lippia* plant named 'ECOLOPIA3' is disclosed, characterized by uniquely long internodes, about 2.9 cm, resulting in tall plants. Plants of the new variety grow vigorously to about 170 cm in 3 months and 5 cm tall. The new variety has excellent tolerance for heat, humidity and disease. Foliage is larger than average, plants are sterile. The new variety is a *Lippia*, useful for a variety of horticultural purposes.

7 Drawing Sheets

Latin name of the genus and species: *Lippia nodiflora*.
Variety denomination: 'ECOLOPIA3'.

BACKGROUND OF THE INVENTION

The new *Lippia* cultivar is a product of chance discovery by the inventor, Masataka Ohde, in Oyama, Japan. The new variety was discovered as a naturally occurring single plant mutation in a greenhouse in Oyama, Japan.

The parent is an unnamed, unpatented variety of *Lippia nodiflora*. The new variety was discovered May of 2018 by the inventor in a group of plants of the parent variety.

Asexual reproduction of the new cultivar 'ECOLOPIA3' was first performed at a commercial greenhouse in Oyama, Japan by terminal vegetative cuttings during June 2018. More than 3 generations have been reproduced by vegetative cuttings. Subsequently, propagation has also shown that the unique features of this cultivar are stable and reproduced true to type.

SUMMARY OF THE INVENTION

The cultivar 'ECOLOPIA3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ECOLOPIA3'. These characteristics in combination distinguish 'ECOLOPIA3' as a new and distinct *Lippia* cultivar:

1. Long internode of about 2.9 cm.
2. Tolerance to disease.
3. Tolerance to high humidity.
4. Above average height of around 5 cm.
5. Above average foliage size
6. Variety is sterile.
7. Rapid growth.

PARENT COMPARISON

Plants of the new cultivar 'ECOLOPIA3' are similar to the parent variety in most horticultural characteristics. The new variety however differs in the following characteristics:

1. Taller plant height, measured at foliar plane; the parent grows to 1.8 cm, the new variety to 5 cm.
2. Internodes of the new variety average 2.9 cm, internodes of the parent average 1.6 cm.
3. The new variety is faster growing than the parent variety.
4. Leaf length of the new variety is about 2 cm, leaf length of the parent is about 1.1 cm.
5. Peduncles of the new variety are about 5 cm, peduncles of the parent are about 2.1 cm.
6. Leaf width of the new variety is about 1.2 cm, leaf width of the parent is about 0.8 cm.

COMMERCIAL COMPARISON

Plants of the new cultivar 'ECOLOPIA3' are similar to the commercial variety *Lippia* 'Campagna Verde' U.S. Plant Pat. No. 20,120 in most horticultural characteristics. The new variety however differs in the following characteristics:

1. Taller plant height, measured at foliar plane. 'Campagna Verde' grows to 3 cm, the new variety to 5 cm.
2. Stronger tolerance to disease under high heat and high humidity conditions.
3. Corolla color of 'Campagna Verde' is Violet-Blue 91D, corolla color of 'ECOLOPIA3' is White 155D.

'ECOLOPIA3' can be compared to the commercial variety *Lippia nodiflora* 'ECOLOPIA1'. Plants of 'ECOLOPIA1' are similar to plants of 'ECOLOPIA3' in most horticultural characteristics. However, 'ECOLOPIA3' differs from *Lippia nodiflora* in the following characteristics:

1. Taller plant height, measured at foliar plane; 'ECOLOPIA1' grows to 1.9 cm, the new variety to 5 cm.
2. Internodes of the new variety average 2.9 cm, internodes of 'ECOLOPIA1' average 1.7 cm.
3. Leaf length of the new variety is about 2 cm, leaf length of 'ECOLOPIA1' is about 1 cm.
4. Leaf width of the new variety is about 1.2 cm, leaf width of 'ECOLOPIA1' is about 0.7 cm.

5. Peduncles of the new variety are about 5 cm, peduncles of 'ECOLOPIA1' are about 2.5 cm.

BRIEF DESCRIPTION OF THE PHOTOGRAPHS

The accompanying photograph in FIG. 1 illustrates in full color a close up view of typical flowers and foliage of a plant of 'ECOLOPIA3' grown outdoors in Oyama, Japan.

Figure 1:
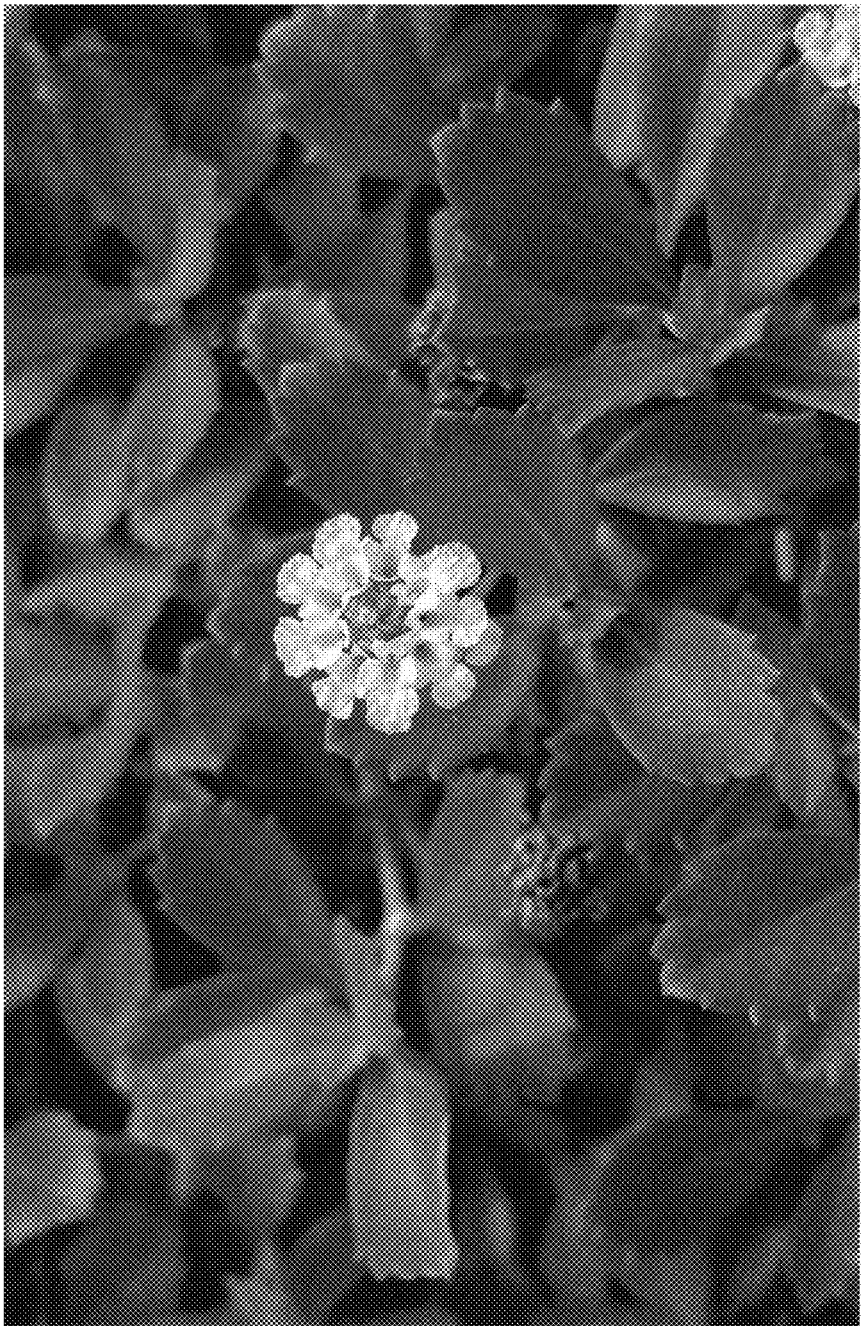
Figure 2:
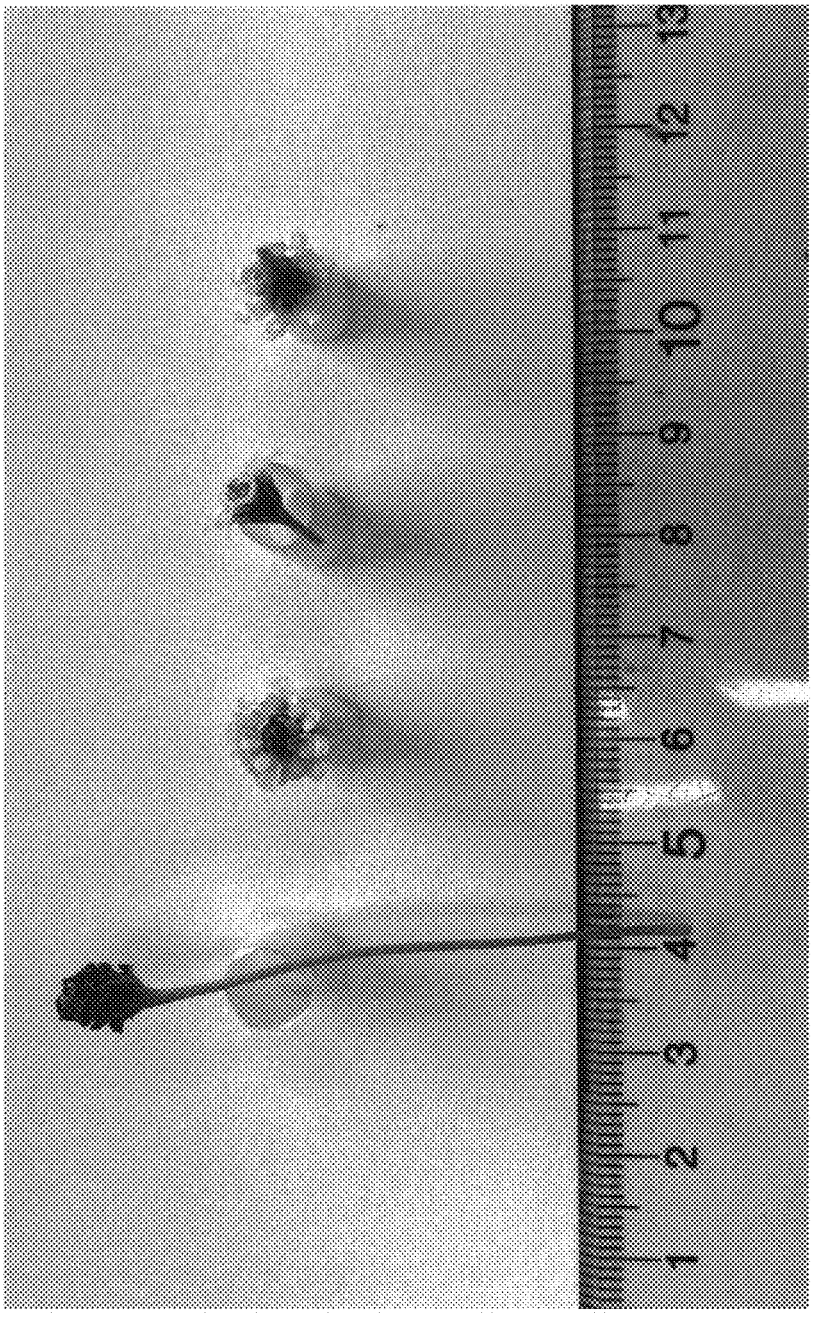
FIG. 2 illustrates a close-up view of a typical inflorescence, with a centimeter ruler for scale.
Figure 3:
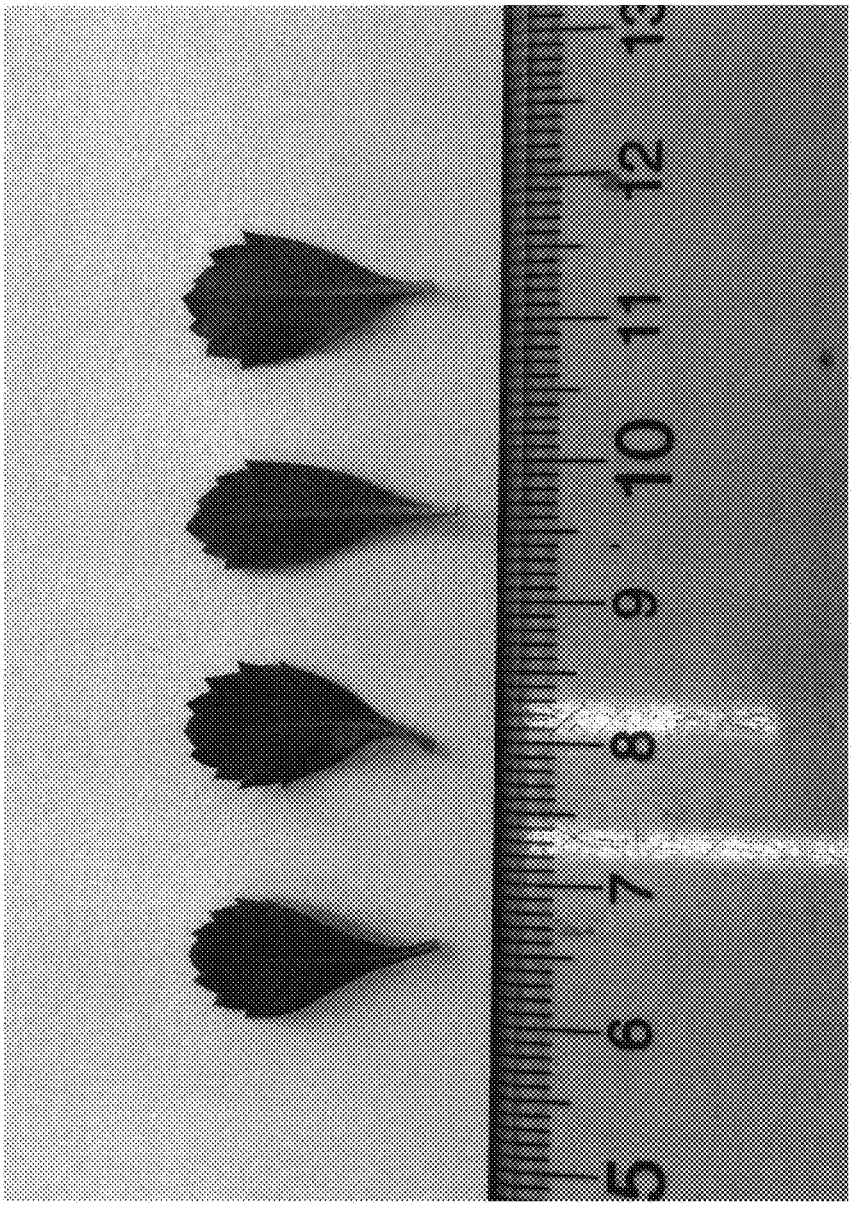
FIG. 3 illustrates a close-up view of foliage, with a centimeter ruler for scale.
Figure 4:
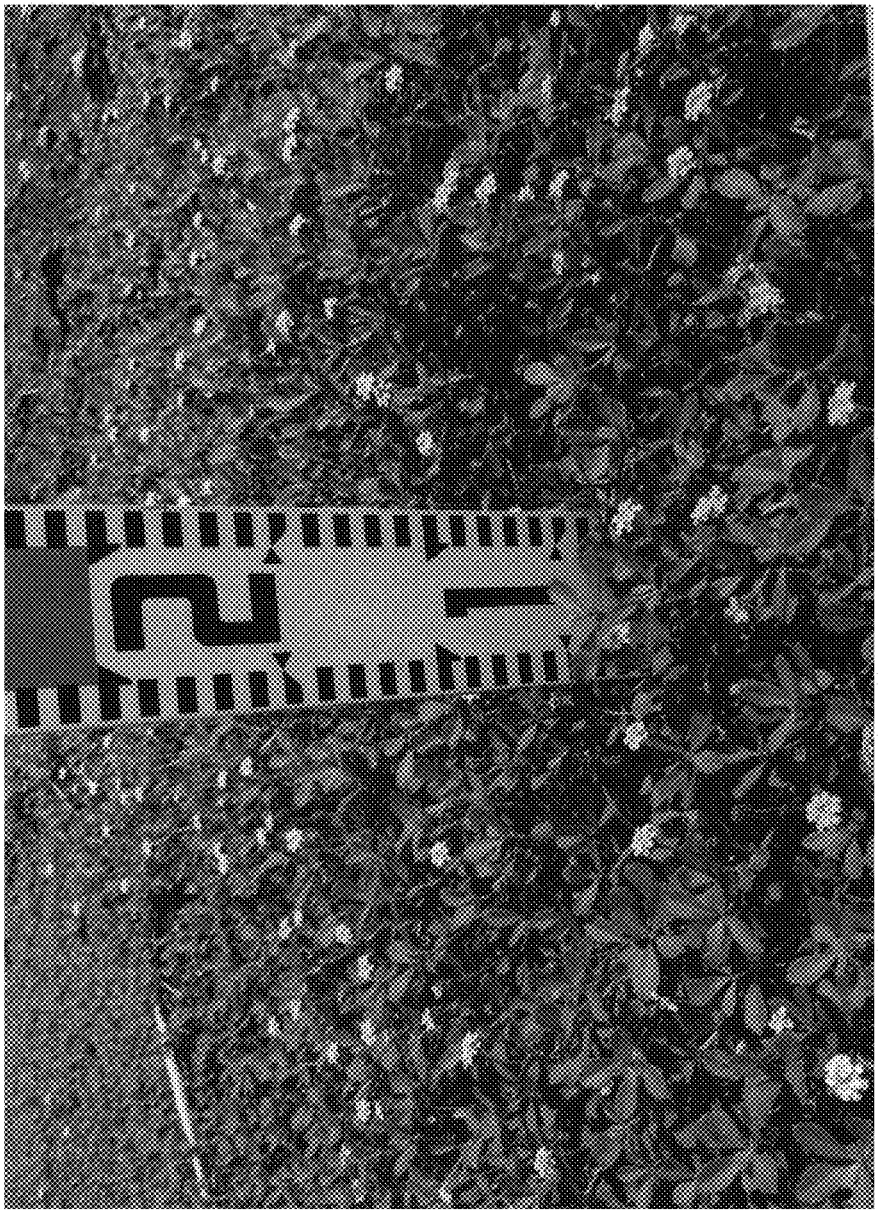
FIG. 4 illustrates a mass planting view of the plant grown outdoors.
Figure 5:
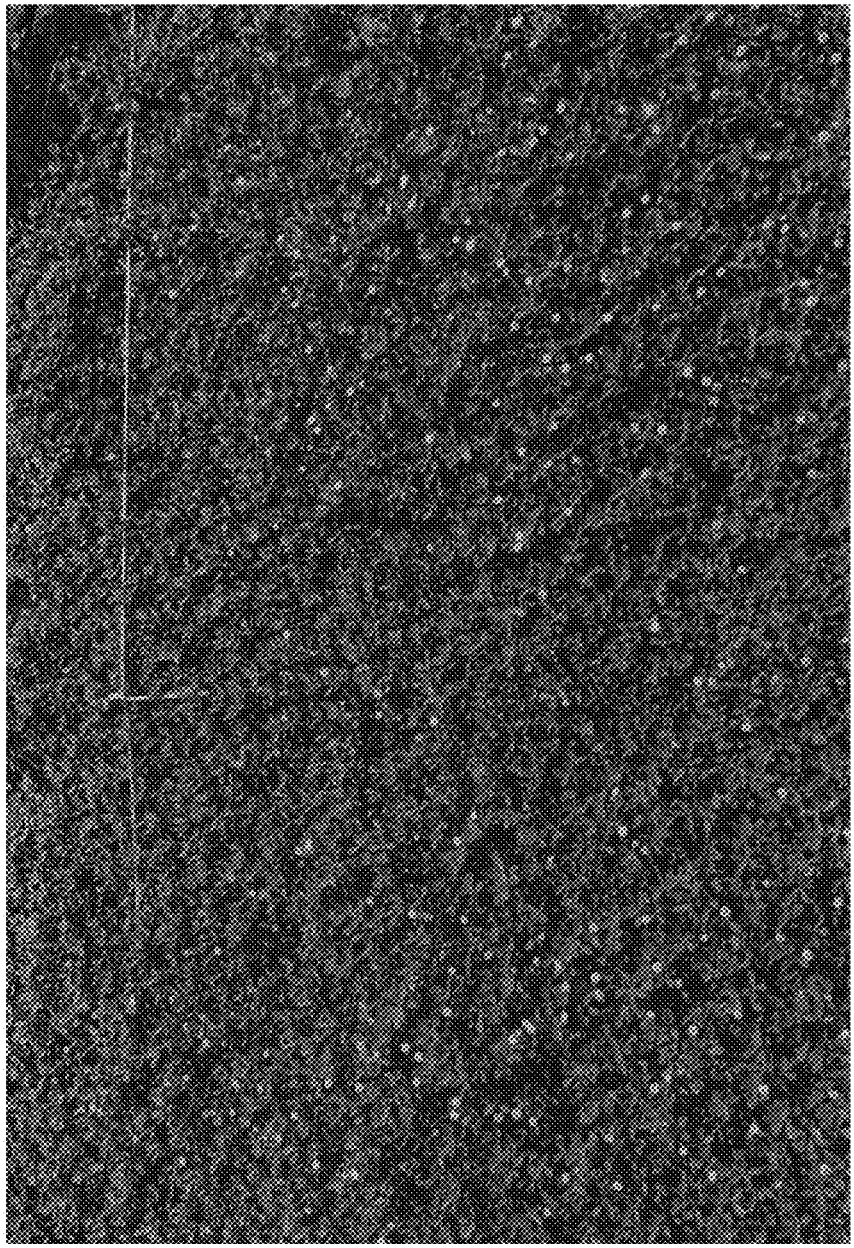
FIG. 5 is a different illustration of 'ECOLOPIA3' plants, grown in a field at 3 months old, already forming a mat.
Figure 6:
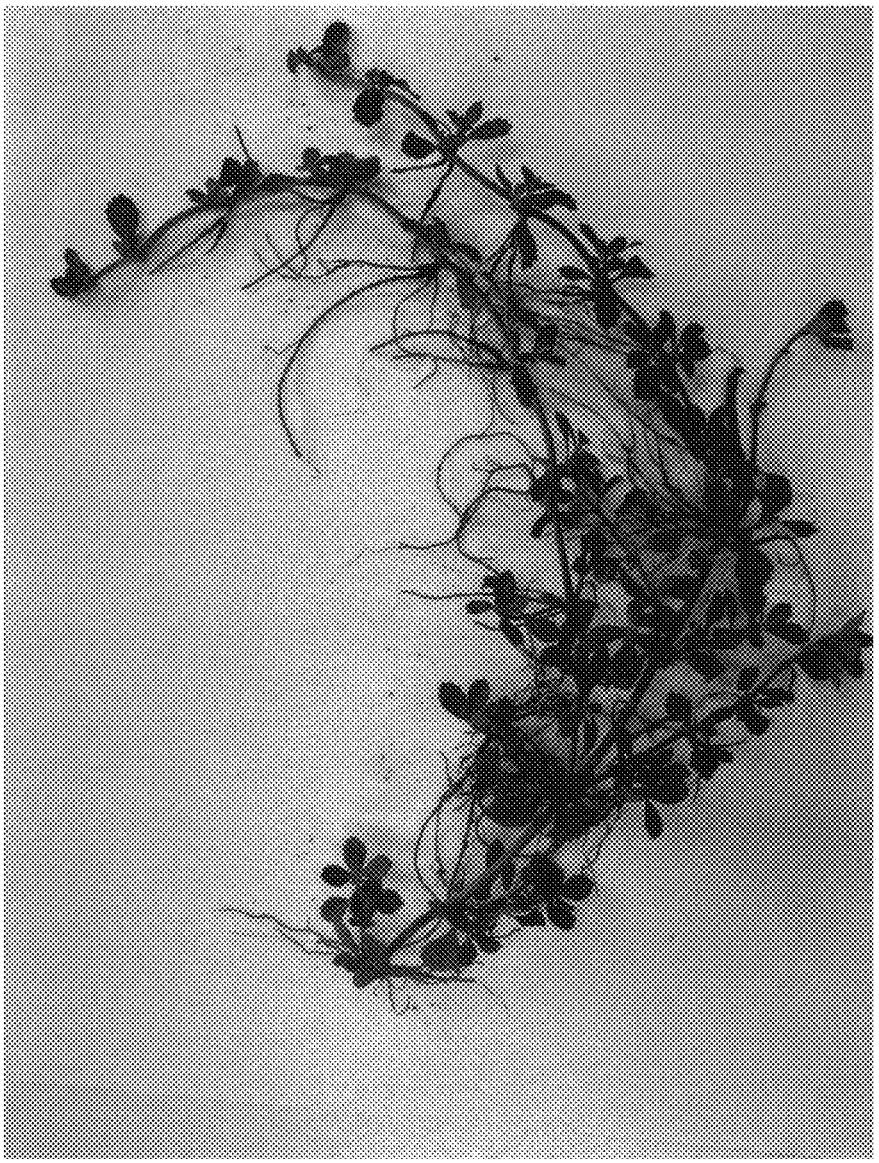
FIG. 6 illustrates a piece of the 3 month old plant, with nodes rooting.
Figure 7:
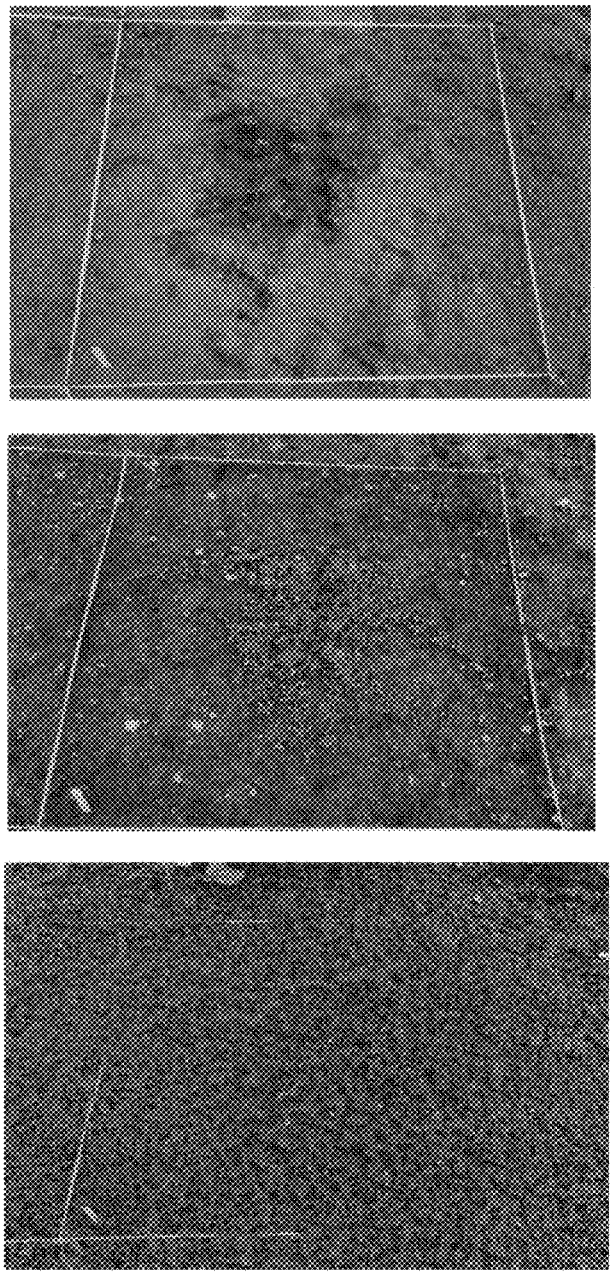
FIG. 7 illustrates plants of 'ECOLOPIA3' at 3 different stages.

Plants on the top of the figure have just been planted, plants in the center of 1 month old, plants on the bottom of the figure are 3 months old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'ECOLOPIA3' plants grown both outdoors and in a temperature controlled greenhouse in Oyama, Japan. Temperatures ranged from −7° C. to 25° C. at night to 3° C. to 50° C. during the day. No artificial light, photoperiodic treatments were given to the plants. Plants were grown both outside research field with plowed soil supplemented with fertilizer containing 8% N, 8% P, and 8% K, and in temperature-controlled and uncontrolled greenhouses in a mixture of Kanuma soil, peat and vermiculite supplemented with the same fertilizer. Measurements and numerical values represent averages of typical plant types.

Botanical classification: *Lippia nodiflora* 'ECOLOPIA3'.

PROPAGATION

Time to initiate roots: 3 to 7 days at approximately 20° C.

Root description: Thin root stretching to downward reaching as deep as 3 feet or deeper with sandy soil.

PLANT

Age of plant described: Approximately 87 days from rooted cutting.

Time of year: Late Summer to early Fall.

Growth habit: Creeping, creating a dense mat.

Planting description: Outdoor field.

Height: 5 cm.

Plant spread: 170 cm diameter, 87 days after planning a rooted cutting, June 2020.

Growth rate: Very fast. 170 cm diameter plant in 3 months from a rooted cutting, during the warm season.

Branching characteristics: Dense, mat forming.

Length of primary lateral branches: Average range 25 to 75 cm during the warm season at 3 months of age from rooted plugs.

Diameter of lateral branches: 5 mm.

Quantity of primary lateral branches: The plant continuously forms branches, approximately 2 to 4 per linear cm.

Characteristics of primary lateral branches:

*Form.*—Round.

*Diameter.*—5 mm.

*Color.*—RHS 177B as stem color.

*Texture.*—Slightly scaly.

*Strength.*—Very strong, difficult to break.

Internode length: 2.9 cm.

FOLIAGE

Leaf:

*Arrangement.*—Opposite.

*Average length.*—2.0 cm.

*Average width.*—1.2 cm.

*Shape of blade.*—Obovate.

*Apex.*—Broad acute.

*Base.*—Attenuate.

*Margin.*—Serrate.

*Texture of top surface.*—Glabrous.

*Texture of bottom surface.*—Glabrous.

*Aspect.*—Nearly flat.

*Color.*—Young foliage upper(front) Near RHS Green 137C. Young foliage under(back) side: Near RHS Green 137D. Mature foliage upper side: Near RHS Green 137C. Mature foliage under side: Near RHS Green 137D.

*Venation.*—Type: Pinnate. Venation color upper side: Near RHS Green 138D. Venation color under side: Near RHS Green 138D.

*Petiole.*—Leaves sessile.

FLOWER

Natural flowering season: May to September.

Days to flowering from rooted cutting: 1-2 months, depend on temperature and light conditions.

Inflorescence and flower type and habit: Terminal head, cluster of sessile flowers.

Rate of flower opening: 8 to 10 days from bud to fully opened flower.

Flower Longevity on plant: about 15 days.

Persistent or self-cleaning: Persistent.

Bud:

*Shape.*—Ovate.

*Length.*—0.6 cm.

*Diameter.*—0.4 cm.

*Color.*—Near RHS Purple 79D.

Inflorescence:

*Depth.*—0.8 cm.

*Diameter.*—1.0 cm.

*Average quantity of individual flowers per inflorescence.*—40.

Corolla:

Individual flower.

*Depth.*—0.6 cm.

*Diameter.*—0.4 cm.

*Petals/lobes.*—Number: 1 fully formed petal. 1 lobed and undeveloped petal of less than 1 mm by 1 mm. Length: 0.5 cm. Width: 0.3 cm. Shape: Tube, flaring open at very end. Apex: Blunt round. Base: Fused.

Margin: Ruffled at apex. Texture: Glabrous all surfaces. Color: When opening: Upper surface: Near RHS Purple 76D. Lower surface: Near RHS Purple 76D. Fully opened: Upper surface: RHS White NN155D. Lower surface: RHS White NN155D.

*Throat.*—Color: Near RHS Yellow 11D. Texture: Glabrous.

*Tube.*—Interior Tube color: Near RHS Yellow 11A. Exterior Tube color: Near RHS Yellow 11D. Texture: Glabrous.

Calyx:

*Form.*—Fused into a tube.

*Length.*—0.3 cm.

*Diameter.*—0.2 cm.

*Texture.*—Glabrous.

*Color.*—Upper surface: Near RHS Green 137D. Lower surface: Near RHS Green 137D.

Fragrance: None.

Pedicels: Not present.

Peduncles:

*Length.*—5.0 cm.

*Diameter.*—0.1 cm.

*Color.*—Near RHS Green 139C.

*Texture.*—Glabrous.

REPRODUCTIVE ORGANS

Stamens:

*Number* (*per flower*).—4.

*Filament length.*—0.05 cm. Anthers: Shape: Linear. Length: 0.05 cm. Color: Near RHS Yellow 13A. Pollen: Scant. Colored Yellow 13B.

Pistils:

*Quantity per flower.*—1. Minute, not measurable.

OTHER CHARACTERISTICS

Seeds and fruits: Plants are sterile.

Disease/pest resistance: Excellent resistance to common diseases of *Lippia nodiflora*. New variety has better resistance to disease under humid and hot conditions than parents. The most common pathogens found in *Lippia* are fungus, including *Puccinia* and *Colletrotrichum*. No particular pest resistance observed.

Temperature tolerance: Plant of the new hybrid have shown excellent resistance to high and low temperature extremes, having been grown successfully under temperature conditions ranging from a gentle frost outdoors, just below 0 degrees Celsius, to 50 degrees Celsius in an uncontrolled greenhouse.

Physical durability: New variety has excellent tolerance to be foot traffic.

Soil pH: New variety has excellent tolerance to a range of soil pH from 4.0-12.0.

What is claimed is:

1. A new and distinct cultivar of *Lippia* plant named 'ECOLOPIA3' as herein illustrated and described.

* * * * *